United States Patent [19]

Shimizu et al.

[11] Patent Number: 4,668,397

[45] Date of Patent: May 26, 1987

[54] NOVEL CYCLIC OCTAPEPTIDE, METHOD FOR PRODUCTION OF SAID OCTAPEPTIDE, AND ION EXTRACTING/SEPARATING AGENT USING SAID OCTAPEPTIDE AS PRINCIPAL COMPONENT

[75] Inventors: Toshimi Shimizu; Yoshio Tanaka, both of Ibaraki, Japan

[73] Assignees: Agency of Industrial Science & Technology; Ministry of International Trade & Industry, both of Tokyo, Japan

[21] Appl. No.: 767,846

[22] Filed: Aug. 21, 1985

[30] Foreign Application Priority Data

Aug. 31, 1984 [JP]  Japan .................................. 59-182966

[51] Int. Cl.$^4$ .......................... B01D 11/00; C07K 5/12
[52] U.S. Cl. ..................................... 210/634; 423/181; 530/321
[58] Field of Search ............... 530/317, 321; 423/181; 210/634

[56] References Cited

U.S. PATENT DOCUMENTS 4,285,857  8/1981  Chipens ............................ 530/317
4,439,359  3/1984  Holy et al. ....................... 530/321
4,486,415  12/1984  Freidinger ....................... 530/317
4,517,122  5/1985  Tomalia et al. .................. 530/317

OTHER PUBLICATIONS

The Peptides, vol. I (1965) 96-109.

*Primary Examiner*—Delbert R. Phillips
*Attorney, Agent, or Firm*—Oblon, Fisher, Spivak, McClelland & Maier

[57] ABSTRACT

Cyclic octapeptide represented by the general formula:

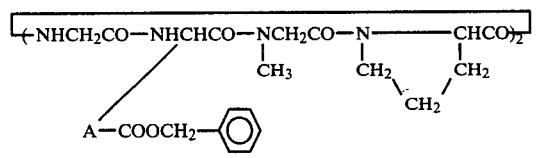

(wherein A denotes an iminoalkylene group of 3 or 4 carbon atoms or an alkylene group of 1 or 2 carbon atoms) are novel substances. They are produced by cyclo-dimerizing specific tetrapeptide esters. They are possessed of excellent properties as an agent for the extraction of ions, particularly alkaline earth metal ions.

22 Claims, No Drawings

NOVEL CYCLIC OCTAPEPTIDE, METHOD FOR PRODUCTION OF SAID OCTAPEPTIDE, AND ION EXTRACTING/SEPARATING AGENT USING SAID OCTAPEPTIDE AS PRINCIPAL COMPONENT

BACKGROUND OF THE INVENTION

This invention relates to a novel cyclic octapeptide capable of intramolecularly binding a specific metal ion such as calcium ion or barium ion and consequently forming a complex and transporting, concentrating, and separating the ion, to a method for the production of the octapeptide, to an ion extracting/separating agent using the octapeptide as a principal component, and to a method for the extraction of ions by the use of the octapeptide. As concerns the industrial sectors in which this invention can be applied, it is useful in the analytical chemical industry and inorganic and organic chemical industry for analysis and separation of the aforementioned metal ions, in the synthetic chemical industry for catalysis of interphase transfer of the aforementioned metal ions, and in the medical and welfare fields for supply of the aforementioned metal ions where their presence is beneficial or for removal of the aforementioned metal ions where their presence is detrimental.

Heretofore, synthetic crown compounds and synthetic cryptand compounds have been known as agents effective in the extraction of ions (as mentioned in Michio Hiraoka: "Crown Compounds", p 176, Kodansha Press, Apr. 1, 1978, for example). While these compounds have high affinity for specific alkali metal ions, they exhibit very poor affinity or virtually no affinity for alkaline earth metal ions such as calcium ions and barium ions.

Transfer of an ion species from an aqueous phase (A) containing the ion species to another aqueous phase (B) has heretofore been attained by the method of interposing between the two aqueous phases an organic phase having the aforementioned known ion extracting agent dissolved therein. In accordance with this conventional method, the amount of ions to be transferred into the aqueous phase (B) is small because the ion-extraction capacity of the agent exhibited in the interface between the aqueous phase (A) and the organic phase is very large as compared with the ion-dissociation capacity of the agent in the interface between the organic phase and the aqueous phase (B). This conventional ion extracting agent has the disadvantage that it is not useful as an agent for the separation and recovery of ions because it permits no easy desorption of ions.

The inventor continued a diligent study directed to development of an ion extracting/separating agent high in affinity for alkaline earth metal ions such as calcium ions and barium ions, namely biologically essential metal ions, and excellent in ability to bind such ions and form a complex, extract the ions effectively, and permit ready dissociation of extracted ions. They have consequently found that a novel cyclic octapeptide formed of eight amino acid residues perfectly answers the aforementioned description of the agent. This invention has been perfected based on this discovery.

SUMMARY OF THE INVENTION

To be specific, this invention aims to provide a novel cyclic octapeptide represented by the general formula:

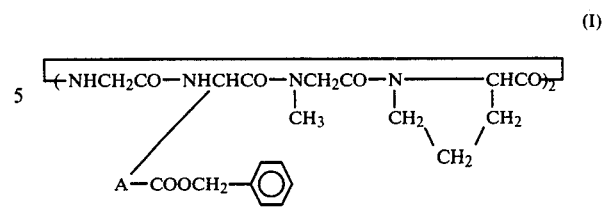

a method for the production of the aforementioned cyclic octapeptide, an ion extracting/separating agent using the cyclic octapeptide as a principal component, and a method for the extraction of ions by the use of the aforementioned cyclic octapeptide.

In the general formula (I), the symbol A denotes an iminoalkylene group of 3 or 4 carbon atoms or an alkylene group of 1 or 2 carbon atoms. Concrete examples of the group include iminopropylene group, iminobutylene group, 1,2-ethylene group, and methylene group.

The compounds represented by this general formula (I) are invariably novel compounds not reported in the literature. They can be produced, for example, by cyclo-dimerizing tetrapeptides represented by the general formula:

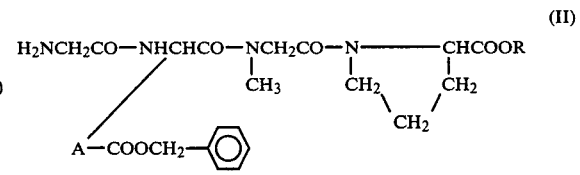

(wherein A denotes an iminoalkylene group of 3 or 4 carbon atoms or an alkylene group of 1 or 2 carbon atoms and R denotes an active ester group).

DESCRIPTION OF THE PREFERRED EMBODIMENTS

First, the method adopted in producing tetrapeptides of the general formula (II) used for the production of octapeptides of the present invention will be described.

For example, a tetrapeptide is obtained by converting sarcosine having a protected amino group into dipeptide through reaction thereof with a L-proline alkyl ester, then removing the amino protecting group from the dipeptide, converting the resultant dipeptide into tripeptide through reaction thereof with L-glutamic acid or L-aspartic acid having the amino group and the side-chain carboxylate group thereof protected or L-lysine or L-ornithine having the two amino groups thereof protected, further removing the tripeptide of the amino protecting group from the tripeptide, then converting the resultant tripeptide into tetrapeptide through reaction thereof with glycine having the amino group thereof protected, subsequently hydrolyzing the alkyl ester moiety at the C terminal of the tetrapeptide thereby converting the moiety into an active ester, and finally removing the tetrapeptide of the amino protecting group at the N terminal of the tetrapeptide.

As the active ester group R in the aforementioned general formula (II), a p-nitrophenyl ester group or a hydroxy succinic acid imide ester group can be used.

As the amino protecting group required in the production of the tetrapeptide of the aforementioned general formula (II), any of the amino protecting groups generally available in the synthesis of peptides can be used. Concrete examples of the amino protecting group include tertiary butyloxycarbonyl group, benzyloxycarbonyl group, p-methoxybenzyloxycarbonyl group, and o-nitrophenylsulfinyl group. As the alkyl ester group for the protection of carboxyl group, a methyl ester group or an ethyl ester group can be used.

The reaction for the formation of peptide bond during the course of the formation of tetrapeptide of the general formula (II) can be effected by suitably combining the conventional methods such as the dicyclohexylcarbodiimide method, active ester method, and mixed acid anhydride method. The peptides obtained as intermediates during the course of production can be easily isolated and purified by being washed with acidic and alkaline aqueous solution and recrystallized.

The tetrapeptide which is the starting material for the octapeptide of this invention is an active ester and is desired to be used in the form of acid salt of the active ester. Examples of the acid salt are hydrochloride, hydrobromide, and hydrofluoride.

The cyclization of the tetrapeptide of the general formula (II) can be carried out in a large volume of an inert solvent such as pyridine or dimethyl formamide at a temperature in the range of 30° to 90° C.

Isolation of the cyclic dimer, i.e. the cyclic octapeptide aimed at by the present invention, from the reaction mixture resulting from the cyclization is effected by subjecting the reaction mixture to vacuum distillation thereby evaporating the solvent, subjecting the residue of distillation to extraction with a mixed solvent of water and alcohol thereby obtaining an extract, treating the extract with an ion-exchange resin thereby removing the unaltered tetrapeptide by adsorption, removing the ion-exchange resin and the solvent from the treated extract thereby obtaining crude cyclic dimers as residue, extracting the crude cyclic dimers as residue with an organic solvent such as methanol thereby obtaining an extract and subjecting the extract to gel filtration using the same solvent as an eluate. The cyclic dimer so isolated may be refined to higher purity by recrystallization when necessary.

The compound of the present invention obtained as described above is such that the actually found elemental analyses thereof agree with the calculated analyses accurately within ±0.3%. In the mass spectrum, this compound gives a parent peak at the position corresponding to the molecular weight. In the infrared absorption spectrum, it shows a characteristic absorption ascribable to the amide bond carbonyl group at 1640 to 1660 cm$^{-1}$. The compound shows a negative ninhydrin reaction. All these data evidence the identity of this compound.

When the cyclic octapeptide of the present invention is dissolved in an organic solvent such as chloroform which is not miscible with water and the resultant solution is mixed with a water phase containing ions, this cyclic octapeptide enables barium ions and calcium ions in the water phase to be extracted into an organic phase several thousand times as efficiently as other monovalent ions such as sodium ions, potassium ions, and rubidium ions. In the transfer of ions by the use of a liquid membrane prepared by dissolving the cyclic octapeptide of this invention in chloroform, calcium ions can be transferred at a higher speed than by the use of A 23187, a naturally occurring ionophore, and separated efficiently from the other ion species.

For practical purposes, the concentration of the cyclic octapeptide of this invention in an organic solvent is desired to fall in the range of $10^{-4}$ to 1 mol/liter.

Now, the present invention will be described more specifically below with reference to working examples. The $R_f$ value by thin-layer chromatography has been determined on the basis that $R_f 1$ represents the value obtained by using a chloroform/methanol (5/1 in volume ratio) mixed solvent as a developing solvent, $R_f 2$ represents the value obtained by using a chloroform/methanol/acetic acid (95/5/1 in volume ratio) mixed solvent as a developing solvent, and $R_f 3$ represents the value obtained by using a n-butanol/acetic acid/water (4/1/2 in volume ratio) mixed solvent as a developing solvent.

REFERENTIAL EXPERIMENT 1

(A) Preparation of tripeptide (ester hydrochloride)

Preparation of $\epsilon$-benzyloxycarbonyl-L-lysyl-sarcosyl-L-proline methyl ester hydrochloride In 100 ml of chloroform, 6.41 g (0.011 mol) of $\alpha$-tertiary butyloxycarbonyl-$\epsilon$-benzyloxycarbonyl-L-lysine dicyclohexylamine salt and 2.70 g (0.011 mol) of sarcosyl-L-proline methyl ester hydrochloride were dispersed. To the resultant dispersion, 3 ml of a solution of 2.35 g (0.011 mol) of dicyclohexylcarbodiimide in chloroform was added at $-10°$ C. Then, the resultant mixture was stirred for reaction at $-10°$ C. for five hours and at room temperature overnight.

The reaction mixture consequently formed was filtered. The filtrate was concentrated under a vacuum. The residue of the concentration was dissolved in 50 ml of ethyl acetate and the resultant solution was filtered. The filtrate was washed with an aqueous 10% citric acid solution, an aqueous 5% sodium hydrogen carbonate solution, and water sequentially in the order mentioned and dried with anhydrous sodium sulfate. The dried substance was distilled under a vacuum to expel the solvent. The residue was solidified with n-hexane to afford 5.05 g of $\alpha$-tertiary butyloxycarbonyl-$\epsilon$-benzyloxycarbonyl-L-lysyl-sarcosyl-L-proline methyl ester (melting point 45° to 48° C., yield 79%). This ester was dissolved in 80 ml of a solution prepared by dissolving dry hydrogen chloride gas in ethyl acetate and adjusting the concentration to 3.5N and then left standing for reaction at room temperature for one hour.

After completion of the reaction, the reaction solution was distilled to expel the solvent. The residue of the distillation was crystallized with diethyl ether to obtain 4.31 g (yield 96.2%) of the compound aimed at.

Physical properties of this compound are shown below.

$R_f$ values of thin-layer chromatography: $R_f 1 = 0.33$, $R_f 2 = 0.33$.

Elemental analyses (as $C_{23}H_{35}O_6N_4Cl \cdot H_2O$)

|  | C | H | N |
|---|---|---|---|
| Calculated (%) | 53.43 | 7.21 | 10.84 |
| Found (%) | 53.64 | 6.99 | 11.06 |

The procedure described above was repeated, except that $\alpha$-tertiary butyloxycarbonyl-$\delta$-benzyloxycarbonyl-L-ornithine dicyclohexylamine salt, $\alpha$-tertiary butyloxycarbonyl-$\gamma$-benzyl-L-glutamic acid dicyclohexylamine salt, and $\alpha$-tertiary butyloxycarbonyl-$\beta$-benzyl-L-aspartic acid dicyclohexylamine salt were used in respective amounts corresponding to 0.011 mol in the place of α-tertiary butyloxycarbonyl-ε-benzyloxycarbonyl-L-lysine dicyclohexylamine salt. Consequently, there were obtained the following compounds.

δ-Benzyloxycarbonyl-L-ornithyl-sarcosyl-L-proline methyl ester hydrochloride (melting point 45° to 47° C.)

γ-Benzyl-L-glutamyl-sarcosyl-L-proline methyl ester hydrochloride (melting point 84° to 85° C.)

β-Benzyl-L-aspartyl-sarcosyl-L-proline methyl ester hydrochloride (melting point 96° to 98° C.)

(B) Preparation of tetrapeptide (ester)

Preparation of tertiary butyloxycarbonylglycyl-ε-benzyloxycarbonyl-L-lysyl-sarcosyl-L-proline p-nitrophenyl ester To 50 ml of a solution of 2.79 g (0.0078 mol) of tertiary butyloxycarbonylglycine dicyclohexylamine salt and 3.96 g (0.0078 mol) of ε-benzyloxycarbonyl-L-lysyl-sarcosyl-L-proline methyl ester hydrochloride in chloroform, 5 ml of a solution of 1.61 g (0.0078 mol) of dicyclohexylcarbodiimide in chloroform was added at −10° C. Thereafter, the resultant mixture was treated by the procedure followed in the preparation of α-tertiary butyloxycarbonyl-ε-benzyloxycarbonyl-L-lysylsarcosyl-L-proline methyl ester in (A) above including such step as stirring at −10° C. for five hours and at room temperature overnight, for example. Consequently, there was obtained 3.55 g (yield 73%) of tertiary butyloxycarbonylglycyl-ε-benzyloxycarbonyl-L-lysyl-sarcosyl-L-proline methyl ester in white solid form having a melting point of 52° to 54° C.

3.32 g of this compound was dissolved in 20 ml of methanol. The resultant solution and 10.72 ml of 1N-NaOH added thereto were left standing for reaction at room temperature for one hour 30 minutes. After completion of the reaction, the reation mixture was mixed with 20 ml of water and distilled under a vacuum to expel methanol. The aqueous solution remaining after the evaporation of methanol was washed with ether and then adjusted to pH 3 to 4 with an aqueous 10% citric acid solution to afford an oily substance. When this oily substance was solidified with petroleum ether, there was obtained 2.91 g (yield 90%) of tertiary butyloxycarbonylglycyl-ε-benzyloxycarbonyl-L-lysyl-sarcosyl-L-proline having a melting point of 76° to 80° C.

A solution of 2.71 g of this compound and 0.69 g of p-nitrophenol in 15 ml of chloroform and 3 ml of a solution of 1.02 g of dicyclohexylcarbodiimide in chloroform added thereto at 0° C. were stirred overnight at 3° C. for reaction. After completion of the reaction, the reaction mixture was filtered and the filtrate was concentrated under a vacuum. The residue was dissolved in 5 ml of acetone containing two drops of acetic acid. The solution was filtered to remove insolubles and the filtrate was freed of the solvent. Consequently, there was obtained an oily substance. By crystallizing this oily substance with ether, there was obtained 3.30 g (yield 100%) of the target product having a melting point of 54° to 56° C. Physical properties of this product are shown below.

$R_f$ value of thin-layer chromatography $R_f1=0.80$, $R_f2=0.31$.

Elemental analyses (as $C_{35}H_{46}O_{11}N_6 \cdot \frac{1}{2}H_2O$)

|  | C | H | N |
|---|---|---|---|
| Calculated (%) | 57.13 | 6.44 | 11.42 |

-continued

|  | C | H | N |
|---|---|---|---|
| Found (%) | 57.08 | 6.41 | 11.13 |

The procedure described above was repeated, except that δ-benzyloxycarbonyl-L-ornithyl-sarcosyl-L-proline methyl ester hydrochloride, γ-benzyl-L-glutamyl-sarcosyl-L-proline methyl ester hydrochloride, and β-benzyl-L-aspartyl-sarcosyl-L-proline methyl ester hydrochloride were used in amounts corresponding to 0.078 mol in the place of ε-benzyloxycarbonyl-L-lysyl-sarcosyl-L-proline methyl ester hydrochloride. Consequently, there were obtained the following compounds satisfying the aforementioned general formula II.

Tertiary butyloxycarbonylglycyl-δ-benzyloxycarbonyl-L-ornithyl-sarcosyl-L-proline p-nitrophenyl ester (melting point 42° to 44° C.)

Tertiary butyloxycarbonylglycyl-γ-benzyl-L-glutamyl-sarcosyl-L-proline p-nitrophenyl ester (melting point 51° to 52° C.)

Tertiary butyloxycarbonylglycyl-β-benzyl-L-aspartyl-sarcosyl-L-proline p-nitrophenyl ester (melting point 45° to 47° C.)

EXAMPLE 1

Preparation of cyclo(glycyl-ε-benzyloxycarbonyl-L-lysyl-sarcosyl-L-prolyl)$_2$ (C-1)

3.10 g (0.0043 mol) of tertiary butyloxycarbonylglycyl-ε-benzyloxycarbonyl-L-lysyl-sarcosyl-L-proline p-nitrophenyl ester was treated with 37 ml of a solution prepared by dissolving dry hydrogen chloride gas in ethyl acetate and adjusting the solution to a concentration of 3.5N while cooled with ice water for one hour. The product of this treatment was distilled to expel the solvent. The residue was solidified with ether. Consequently, there was obtained 2.74 g (yield 97%) of glycyl-ε-benzyloxycarbonyl-L-lysyl-sarcosyl-L-proline p-nitrophenyl ester hydrochloride.

This salt was dissolved in 20 ml of dimethyl formamide. The resultant solution was added dropwise into 1300 ml of pyridine at 60° C. over a period of six hours. The mixture was then stirred at 30° C. overnight and at 60° C. for five hours for reaction.

After completion of the reaction, the reaction mixture was freed of the solvent and the residue was dissolved in a mixed solvent of water and methanol. The resultant solution was passed through H$^+$ form and OH$^-$ form ion-exchange resin columns washed in advance with the same solvent, to remove the unaltered reactants. Then the solution was freed of the solvent. The residue was dissolved in methanol and passed through a column packed with Sephadex LH-20 (Farmacia Fine Chemicals Inc's trademark for a substance formed preponderantly of hydroxypropylated dextran) for gel filtration to collect a fraction containing a cyclic dimerization product. The fraction was freed of the solvent and the residue was recrystallized with chloroform-diethyl ether. Consequently, there was obtained 680 mg (yield 70%) of cyclic octapeptide (C-1) having a melting point of 125° to 126° C.

This compound showed a negative ninhydrin reaction, showed absorptions, $\nu_{max}=2950$, 1655, 1530, and 1250 cm$^{-1}$, in the infrared absorption spectrum, and showed M$^+$=975 in the mass spectrum. Physical properties of the compound are as follows.

R_f value of thin-layer chromatography: $R_f1=0.13$, $R_f2=0$, and $R_f3=0.33$.

Elemental analyses (as $C_{48}H_{66}O_{12}H_{10}\cdot 2H_2O$)

|  | C | H | N |
|---|---|---|---|
| Calculated (%) | 57.01 | 6.98 | 13.85 |
| Found (%) | 57.36 | 6.84 | 13.91 |

All the data given above identify the compound to be a cyclic octapeptide (C-1) of the present invention.

EXAMPLE 2

Preparation of cyclo(glycyl-δ-benzyloxycarbonyl-L-ornithyl-sarcosyl-L-prolyl)₂ (C-2)

The procedure of Example 1 was faithfully repeated, except that tertiary butyloxycarbonylglycyl-δ-benzyloxycarbonyl-L-ornithyl-sarcosyl-L-proline p-nitrophenyl ester was used in an amount corresponding to 0.0043 mol in the place of tertiary butyloxycarbonylglycyl-δ-benzyloxycarbonyl-L-lysyl-sarcosyl-L-proline p-nitrophenyl ester. Consequently, there was obtained 340 mg (yield 26%) of a cyclic octapeptide (C-2) having a melting point of 100° to 101° C.

This compound showed a negative ninhydrin reaction, showed absorptions, $\nu_{max}=2950$, 1650, and 1530 cm$^{-1}$, in the infrared absorption spectrum, and showed M$^+=947$ in the mass spectrum. Physical properties of the compound were as follows.

R_f value of thin-layer chromatography: $R_f1=0.11$, $R_f2=0$, and $R_f3=0.30$.

Elemental analyses (as $C_{46}H_{62}O_{12}N_{12}\cdot H_2O$)

|  | C | H | N |
|---|---|---|---|
| Calculated (%) | 57.25 | 6.68 | 14.51 |
| Found (%) | 57.41 | 6.52 | 14.75 |

EXAMPLE 3

Preparation of cyclo(glycyl-γ-benzyl-L-glutamylsarcosyl-L-prolyl)₂ (C-3)

The procedure of Example 1 was repeated, except that tertiary butyloxycarbonylglycyl-γ-benzyl-L-glutamylsarcosyl-L-proline p-nitrophenyl ester in an amount corresponding to 0.0043 mol was used in the place of tertiary butyloxycarbonylglycyl-δ-benzyloxycarbonyl-L-lysyl-sarcosyl-L-proline p-nitrophenyl ester. Consequently, there was obtained 190 mg (yield 16%) of a cyclic octapeptide (C-3) having a melting point of 157° to 159° C.

This compound showed a negative ninhydrin reaction, showed absorption, $\nu_{max}=1660$ and 1530 cm$^{-1}$, in the absorption spectrum, and showed M$^+=889$ in the mass spectrum. Physical properties of this compound were as follows.

R_f value of thin-layer chromatography: $R_f1=0.18$, $R_f2=0$, and $R_f3=0.41$.

Elemental analyses (as $C_{44}H_{56}O_{12}N_8O$).

|  | C | H | N |
|---|---|---|---|
| Calculated (%) | 58.27 | 6.45 | 12.35 |
| Found (%) | 58.51 | 6.23 | 12.44 |

EXAMPLE 4

Preparation of cyclo(glycyl-β-benzyl-L-aspartylsarcosyl-L-prolyl)₂ (C-4)

The procedure of Example 1 was repeated, except that tertiary butyloxycarbonylglycyl-β-benzyl-L-aspartyl-sarcosyl-L-proline p-nitrophenyl ester was used in an amount corresponding to 0.0043 mol in the place of tertiary butyloxycarbonylglycyl-δ-benzyloxycarbonyl-L-lysyl-sarcosyl-L-proline p-nitrophenyl ester. Consequently, there was obtained 230 mg (yield 20%) of a cyclic octapeptide (C-4) having a melting point of 138° to 139° C.

This compound showed a negative ninhydrin reaction, showed absorptions, $\nu_{max}=1660$ and 1530 cm$^{-1}$, in the infrared absorption spectrum, and M$^+=861$ in the mass spectrum. Physical properties of the compound were as follows.

R_f value of thin-layer chromatography: $R_f1=0.17$, $R_f2=0$, and $R_f3=0.40$.

Elemental analyses (as $C_{42}H_{52}O_{12}N_8\cdot\frac{1}{2}H_2O$)

|  | C | H | N |
|---|---|---|---|
| Calculated (%) | 57.99 | 6.14 | 12.88 |
| Found (%) | 58.33 | 6.09 | 12.95 |

EXAMPLE 5

The compound (C-1) of this invention obtained in Example 1 was dissolved in concentrations of 140, 280, 420, 560, and 700 mM in chloroform. Then 5-ml portions of each of the five solutions so prepared were mixed one each with 5-ml aqueous solutions (pH 7.4) of metallic ion chloride (10 mM), picric acid (25 mM), and good buffer HEPES (10 mM) and shaken for 30 minutes. The shaken mixtures were left stading for one hour. Then, based on the absorbance of picrate anion in the chloroform phase, the extraction equilibrium constants of the compound (C-1) of this invention for the various ions were determined. The results so obtained were compared with those of the comparative cyclic tetrapeptide, i.e. cyclo(glycyl-ε-benzyloxycarbonyl-L-lysyl-sarcosyl-L-prolyl) (D-1), and the linear octapeptide, i.e. tertiary butyloxycarbonylglycyl-ε-benzyloxycarbonyl-L-lysyl-sarcosyl-L-prolylglycyl-ε-benzyloxycarbonyl-L-sarcosyl-L-proline methyl ester (E-1).

The results expressed as logarithms of the average values obtained by using the five chloroform solutions of varying concentration are shown in Table 1.

It is noted from this table that while the comparative compounds showed virtually no extracting ability to such alkaline earth metal ions as calcium ions and barium ions, the compounds of this invention showed extremely high extracting ability to such ions. They showed particularly high extracting ability especially to alkaline earth metal ions.

TABLE 1

| | Logarithm of ion extraction equilibrium constant Compound | | |
|---|---|---|---|
| | Example | Comparative Experiment | |
| Ion | C-1 | D-1 | E-1 |
| Na$^+$ | 2.3 | 1.1 | 0.9 |
| K$^+$ | 2.6 | 1.2 | 0.9 |
| Rb$^+$ | 2.6 | 1.2 | 0.9 |
| Mg$^{2+}$ | 3.4 | 1.2 | 0.9 |

TABLE 1-continued

| | Logarithm of ion extraction equilibrium constant Compound | | |
|---|---|---|---|
| | Example | Comparative Experiment | |
| Ion | C-1 | D-1 | E-1 |
| $Ca^{2+}$ | 5.6 | 1.7 | 1.1 |
| $Ba^{2+}$ | 6.0 | 1.9 | 1.3 |

EXAMPLE 6

In a U-shaped tube 15 mm in inside diameter, two water phases (a), (b) (each 10 ml) were separated by an intervening chloroform phase (15 ml). In the water phase (a), a chloride of potassium ions and calcium ions (10 mM), picric acid (25 mM), and good buffer HEPES (10 mM) were dissolved and adjusted to pH 7.5 with lithium hydroxide. In the chloroform phase, the compound of this invention was dissolved in a concentration of 200 μM. The two water phases (a), (b) were stirred with a mechanical stirrer and the chloroform phase was stirred with a magnetic stirrer. After 10 hours of stirring, the amount of potassium ions or calcium ions which had been transferred from the water phase (a) through the chloroform phase into the water phase (b) was determined based on the absorption of picrate anion. For comparison, the procedure described above was repeated by using a naturally occurring calcium-ion ionophore A 23187, the cyclic tetrapeptide, i.e. cyclo(g-lycyl-ε-benzyloxycarbonyl-L-lysyl-sarcosyl-L-prolyl) (D-1), the linear octapeptide, i.e. tertiary butyloxycarbonylglycyl-ε-benzyloxycarbonyl-L-lysyl-sarcosyl-L-propyl-glycyl-ε-benzyloxycarbonyl-L-lysyl-sarcosyl-L-proline methyl ester (E-1), and using no substance dissolved in the chloroform phase. The results are shown in Table 2.

It is noted from this table that virtually no transferring ability for potassium ion or calcium ion was obtained where the comparative compounds D-1 and E-1 were used and where nothing was dissolved in the chloroform phase, whereas the compounds of this invention transferred calcium ions in a form separated from potassium ions more efficiently than the natural substance A 23187.

TABLE 2

| | Amount of ions transferred (μ · mol) | |
|---|---|---|
| Compound | K | $Ca^{2+}$ |
| Example | | |
| C-1 | 0.5 | 5.4 |
| C-2 | 0.4 | 5.1 |
| C-3 | 0.3 | 4.9 |
| C-4 | 0.3 | 4.8 |
| Comparative Example | | |
| A23187 | 0.1 | 4.7 |
| D-1 | 0.1 | 0.4 |
| E-1 | 0.2 | 0.3 |
| None | 0 | 0 |

EXAMPLE 7

The amount 100 ml of chloroform solution having dissolved therein 1 g of the compound (C-1) of this invention obtained in Example 1 and 100 ml of a sample solution containing 1 g of magnesium picrate and 100 mg of potassium picrate (adjusted to pH 6.9 with acetic acid and sodium acetate) were thoroughly shaken and then left standing for 30 minutes. From the resultant mixture, the chloroform phase was collected. The chloroform phase was washed with 100 ml of an aqueous solution containing 0.01M of lithium picrate (adjusted to pH 6.9 with acetic acid and sodium acetate), followed by collection of chloroform phase. This washing operation was repeated three times to collect the chloroform phase. This chloroform phase was thoroughly shaken with 100 ml of an aqueous solution containing 2M of ammonium chloride and 2M of hydrochloric acid. The shaken mixture was left standing at rest for 30 minutes, followed by collection of the aqueous phase. The aqueous phase was tested for recovery of calcium ion. The recovery ratio was found to be 95%. At that time, the concentration of magnesium was $10^{-3}$ times the initial concentration. Thus, by the method of solution extraction using the compound of this invention, calcium ions could be efficiently separated from a large amount of magnesium ions.

What is claimed is:

1. A cyclic octapeptide represented by the formula:

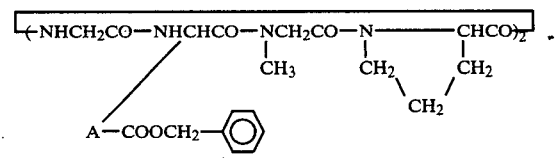

wherein A denotes a group selected from the group consisting of iminoalkylene groups of 3 or 4 carbon atoms and alkylene groups of 1 or 2 carbon atoms.

2. The cyclic octapeptide according to claim 1, wherein A is an iminopropylene group.

3. The cyclic octapeptide according to claim 1, wherein A is an iminobutylene group.

4. The cyclic octapeptide according to claim 1, wherein A is a methylene group.

5. The cyclic octapeptide according to claim 1, wherein A is an ethylene group.

6. A method of synthesizing a cyclic octapeptide of the formula:

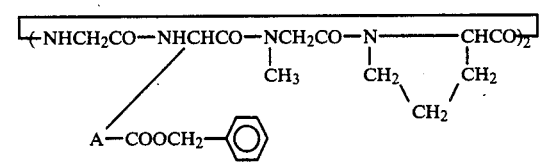

comprising the steps of:

(i) cyclizing a tetrapeptide of the formula:

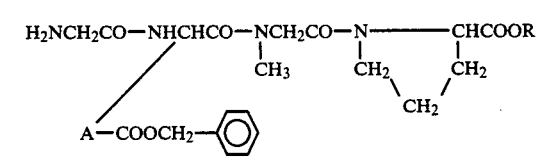

wherein A represents a member selected from the group consisting of iminoalkylene groups of 3 or 4 carbon atoms and alkylene groups of 1 or 2 carbon atoms, and COOR represents an active ester group, in an inert solvent at a temperature ranging from 30° to 90° C. thereby producing a cyclization mixture;

(ii) removing the solvent from said mixture;
(iii) extracting the residue obtained after solvent removal with a mixed solvent of water and an alcohol thereby obtaining an extract;
(iv) treating said etract with an ion exchange resin thereby removing uncyclized tetrapeptide from the extract;
(v) removing said ion-exchange resin and solvent from said treated extract, thereby yielding a residue containing crude cyclic dimers;
(vi) extracting the crude residue obtained in step (v) with an inorganic solvent; and
(vii) subjecting the extract of step (vi) to gel filtration and employing the same solvent of the extract solution being subjected to gel filtration as the eluate of the gel filtration step.

7. The method according to claim 6, wherein A is an iminopropylene group.

8. The method according to claim 6, wherein A is an iminobutylene group.

9. The method according to claim 6, wherein A is a methylene group.

10. The method according to claim 6, wherein A is an ethylene group.

11. An ion extracting/separating agent, comprising a cyclic octapeptide of the formula:

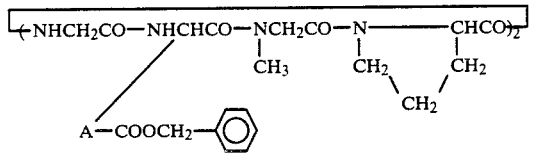

wherein A denotes a group selected from the group consisting of iminoalkylene groups of 3 or 4 carbon atoms and alkylene groups of 1 or 2 carbon atoms, and an organic solvent.

12. The ion extracting/separating agent according to claim 11, wherein A is an iminopropylene group.

13. The ion extracting/separating agent according to claim 11, wherein A is an iminobutylene group.

14. The ion extracting/separating agent according to claim 11, wherein A is a methylene group.

15. The ion extracting/separating agent according to claim 11, wherein A is an ethylene group.

16. The ion extracting/separating agent according to claim 11, wherein the concentration of said cyclic octapeptide in said organic solvent is in the range of $10^{-4}$ to 1 mol/liter.

17. A method for the extraction of an ion selected from the group consisting of alkali metal ion and alkaline earth metal ions from an aqueous solution containing said ion, which comprises:

(a) dissolving a cyclic octapeptide of the formula:

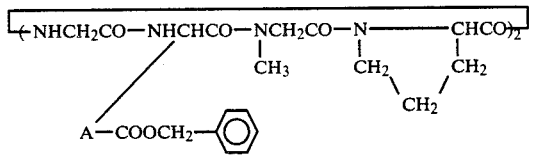

wherein A represents a member selected from the group consisting of an iminoalkylene group of 3 or 4 carbon atoms and an alkylene group of 1 or 2 carbon atoms, in an organic solvent;

(b) mixing the resulting organic solvent solution containing the cyclic octapeptide with an aqueous solution containing one of said ions, thereby extracting said ion into the organic solvent phase as a result of complex formation of the ion with said peptide.

18. The method according to claim 17, wherein A is an iminopropylene group.

19. The method according to claim 17, wherein A is an iminobutylene group.

20. The method according to claim 17, wherein A is a methylene group.

21. The method according to claim 17, wherein A is a ethylene group.

22. The method according to claim 17, wherein the concentration of said cyclic octapeptide in said organic solvent is in the range of $10^{-4}$ to 1 mol/liter.

* * * * *